United States Patent
Bhushan et al.

(10) Patent No.: US 9,512,154 B2
(45) Date of Patent: Dec. 6, 2016

(54) $^{18}$FDG MULTIMERIC POSITRON EMISSION TOMOGRAPHY IMAGING AGENTS

(76) Inventors: Kumar Ranjan Bhushan, St Louis, MO (US); Preeti Misra, St Louis, MO (US)

(*) Notice: Subject to any disclaimer, the term of this patent is extended or adjusted under 35 U.S.C. 154(b) by 1174 days.

(21) Appl. No.: 13/554,037

(22) Filed: Jul. 20, 2012

(65) Prior Publication Data

US 2014/0024803 A1    Jan. 23, 2014

(51) Int. Cl.
*A61K 51/04*    (2006.01)
*C07F 9/30*    (2006.01)
*C07F 9/38*    (2006.01)

(52) U.S. Cl.
CPC ......... *C07F 9/3873* (2013.01); *A61K 51/0491* (2013.01); *C07F 9/301* (2013.01)

(58) Field of Classification Search
CPC ..... A61K 51/0491; C07F 9/301; C07F 9/3873
See application file for complete search history.

(56) References Cited

U.S. PATENT DOCUMENTS

| | | | |
|---|---|---|---|
| 2005/0026864 A1* | 2/2005 | Dixon | A61K 31/675 514/47 |
| 2005/0136001 A1* | 6/2005 | McBride | A61K 47/48246 424/1.11 |
| 2006/0063834 A1* | 3/2006 | Frangioni | C07C 51/15 514/519 |
| 2006/0083678 A1* | 4/2006 | Frangioni | A61K 51/0491 424/1.11 |
| 2006/0239926 A1* | 10/2006 | Port | A61K 49/0002 424/9.363 |
| 2009/0028788 A1* | 1/2009 | Achilefu | A61K 47/48238 424/1.69 |
| 2011/0033379 A1* | 2/2011 | Frangioni | A61K 51/0482 424/1.65 |

* cited by examiner

*Primary Examiner* — Michael G Hartley
*Assistant Examiner* — Leah Schlientz

(57) ABSTRACT

The present invention discloses $^{18}$FDG conjugated positron emission tomography (PET) imaging agents. In particular, the present invention discloses a cancer specific $^{18}$FDG multimeric PET imaging agents.

20 Claims, 9 Drawing Sheets

18FDG MULTIMERIC POSITRON EMISSION TOMOGRAPHY IMAGING AGENTS

FIELD OF THE INVENTION

The present invention discloses a cancer specific $^{18}$FDG multimeric positron emission tomography (PET) imaging agents.

BACKGROUND

Conventional positron emission tomography (PET) scanning relies on the coincident detection of anti-parallel 511 keV gamma rays that arises when anti-matter (a positron) and matter (an electron) annihilate each other. Coincident detection of these anti-parallel gamma rays is accomplished using a stationary ring of detector elements, and various computer algorithms are used to reconstruct the original distribution of isotope. Relative to single photon emission computed tomography (SPECT), PET is dramatically more sensitive (~1% for most clinical PET scanner vs. 0.01% for clinical SPECT scanners) owing in large part to the absence of a collimator. PET also has higher resolution than SPECT, with most clinical scanners providing final reconstructed voxel sizes of 8 mm×8 mm×8 mm (0.5 cm$^3$). Since human body has no naturally occurring positrons, the administration of an appropriate positron-emitting radiotracer permits the quantitative, 3D localization of disease, as well as the study of a variety of functional processes in vivo {Raichle, 1979; Yamamoto, 1984}.

PET has revolutionized the detection and staging of human cancer, however, it is far from reaching its potential. Unfortunately, the term "PET scanning" is presently synonymous with the use of 2-[$^{18}$F]fluoro-2-deoxy-D-glucose ($^{18}$FDG) as the radiotracer. Although valuable as a cancer biomarker, $^{18}$FDG has variable uptake and retention in many tumors {Kelloff, 2005}, as well as high uptake in normal tissues and organs {Kumar, 2006}. In general, there remain two major problems in the field of PET cancer imaging: 1) the difficulty in producing high affinity small molecule ligands specific for particular cancers, and 2) the complex and expensive chemistry infrastructure required for traditional radiolabeling with $^{18}$F.

SUMMARY

Over the last 7 to 8 years, there has been virtual explosion in PET, and now PET/CT scanners are available worldwide. The addition of CT to PET permits attenuation correction and provides anatomical landmarks. A new generation of time-of flight (TOF) PET scanners {Conti, 2005; Surd, 2006} offers a 2-fold improvement in resolution or sensitivity (but not both) and is especially useful for scanning large patients. An even newer advancement is the fusion of PET with magnetic resonance imaging (MRI). Although it is unclear how well these scanners will perform with respect to attenuation correction, their anatomical imaging is outstanding.

Nature often takes advantage of multimerization to decrease ligand off-rate and improve affinity of cell surface binders {Kitov, 2003; Mammen, 1998}. There is a general need to find suitable scaffolds for the assembly of multiple targeting ligands and contrast agents in hope that multimerization would improve the performance of cancer specific ligands.

Several different multivalent scaffolds have been used successfully in past particularly for applications in carbohydrate/lectin interactions {Lindhorst, 2002; Lundquist, 2002} but also for peptide/protein interactions {Wright, 2001} and in context of tumor targeting {Carlson, 2007; Thumshirn, 2003}. Among these scaffolds are small molecules with few conjugation sites (~2-10) and larger systems like dendrimers {Voegtle, 2007} and polymers {Haag, 2006}.

Although $^{18}$FDG has been successful as a PET imaging agents, there is a need for new imaging agents. In particular, there is a need for imaging agents for cancers that are not $^{18}$FDG-avid. For example, $^{18}$FDG-PET has little role in carcinoid, bronchoalveolar carcinoma, lobular breast cancer, prostate cancer, and well-differentiated thyroid cancer. There is also a general need to find more specific imaging agents which can enable better imaging. In short, PET scanner technology is improving at an incredibly rapid rate. Unfortunately, the development of targeted radiotracers for cancer detection is lagging behind.

The present invention describes a development of $^{18}$FDG-based PET multivalent radiotracers for targeted cancer imaging. Ligands are chosen not only for their clinical relevance, but because they represent the extremes of chemical structure, from highly anionic to neutral/zwitterionic, and can therefore be used to validate the robustness of multimeric radiotracer $^{18}$F production.

In one aspect of present invention, a targeting ligand is conjugated with multivalent scaffold followed by deprotection of amino protecting group to generate an amine containing targeting ligand conjugated multivalent scaffold (FIG. 1 and FIG. 2). In such aspect $L_1$ and $L_2$ are linkers independently selected from alkane, amino acid, —NHCO(CH$_2$)$_5$—, polyethylene glycol and polypropylene glycol. R is independently selected from Boc, Fmoc, Ac, Cbz, Bz and Bn. R$^1$, R$^2$ and R$^3$ are targeting ligand or —OH.

In an another aspect of present invention, an amine containing targeting ligand conjugated multivalent scaffold is reacted with a $^{18}$FDG in presence of a reducing agent to yield a multivalent $^{18}$FDG amino conjugated imaging agent (FIG. 3 and FIG. 4).

In an another aspect of present invention, $^{18}$FDG is treated with a bromine water to produce a gluconic acid lactone intermediate followed by a reaction with an amine containing targeting ligand conjugated multivalent scaffold to yield a multivalent $^{18}$FDG amido conjugated imaging agent (FIG. 5 and FIG. 6).

In one embodiment, amino acid is natural amino acid. In some embodiments, amino acid is unnatural amino acid. In some embodiments, an alkane is C0-C20 straight chain carbon unit. In some embodiments, polyethylene glycol is 1 to 20 ethylene glycol unit. In some embodiments, polypropylene glycol is 1 to 20 propylene glycol unit. In some embodiments, targeting ligand is independently selected from bisphosphonates, RGD peptides,

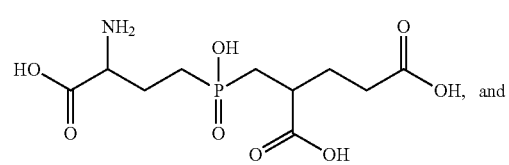

-continued

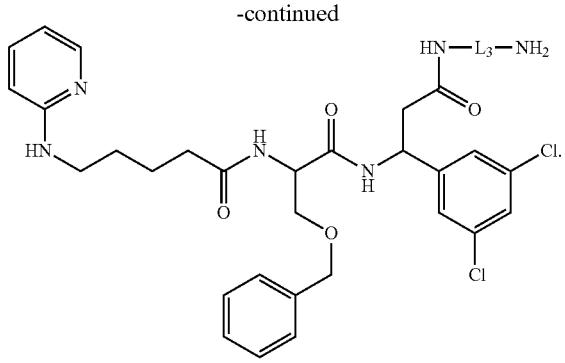

In some embodiments, $L_3$ is a linking moiety independently selected from alkane, polyethylene glycol and polypropylene glycol. In some embodiments, bisphosphonates is selected from alendronate, neridronate, pamidronate, risedronate, tiludronate and zoledronate. In some embodiments, RGD peptides is independently selected from c(RGDfC), c(RADfC), c(RGDfK), c(RADfK), c(RGDfE), c(RADfE), RGDSK, RADSK, RGDS, c(RGDfV), c(RGDyC), c(RADyC), c(RGDyE), c(RGDyK), c(RADyK) and H-E[c(RGDyK)]$_2$.

The present invention describes $^{18}$FDG conjugated PET imaging agents. Particularly, the present invention discloses a cancer specific $^{18}$FDG multimeric small-molecule PET radiotracers. Specifically, bisphosphontes, a multivalent pamidronate $^{18}$FDG conjugated imaging agent have specificity over clinically used Na$^{18}$F.

DETAILED DESCRIPTION

In a present invention, synthetic strategy is developed for $^{18}$FDG-based PET multivalent radiotracers for targeted cancer imaging. Targeting ligand is conjugated with NHS ester of multivalent scaffold and following couple of steps, $^{18}$FDG-based PET multivalent radiotracers are obtained.

The $^{18}$FDG-based PET multivalent radiotracers of present invention are prepared according to the methods known in the art, as illustrated in FIGS. 1-6 and described for specific compounds in examples 1-3. Products are characterized by analytical HPLC, NMR and LCMS, and are obtained in typical yields of 35-45%.

Figure 1:
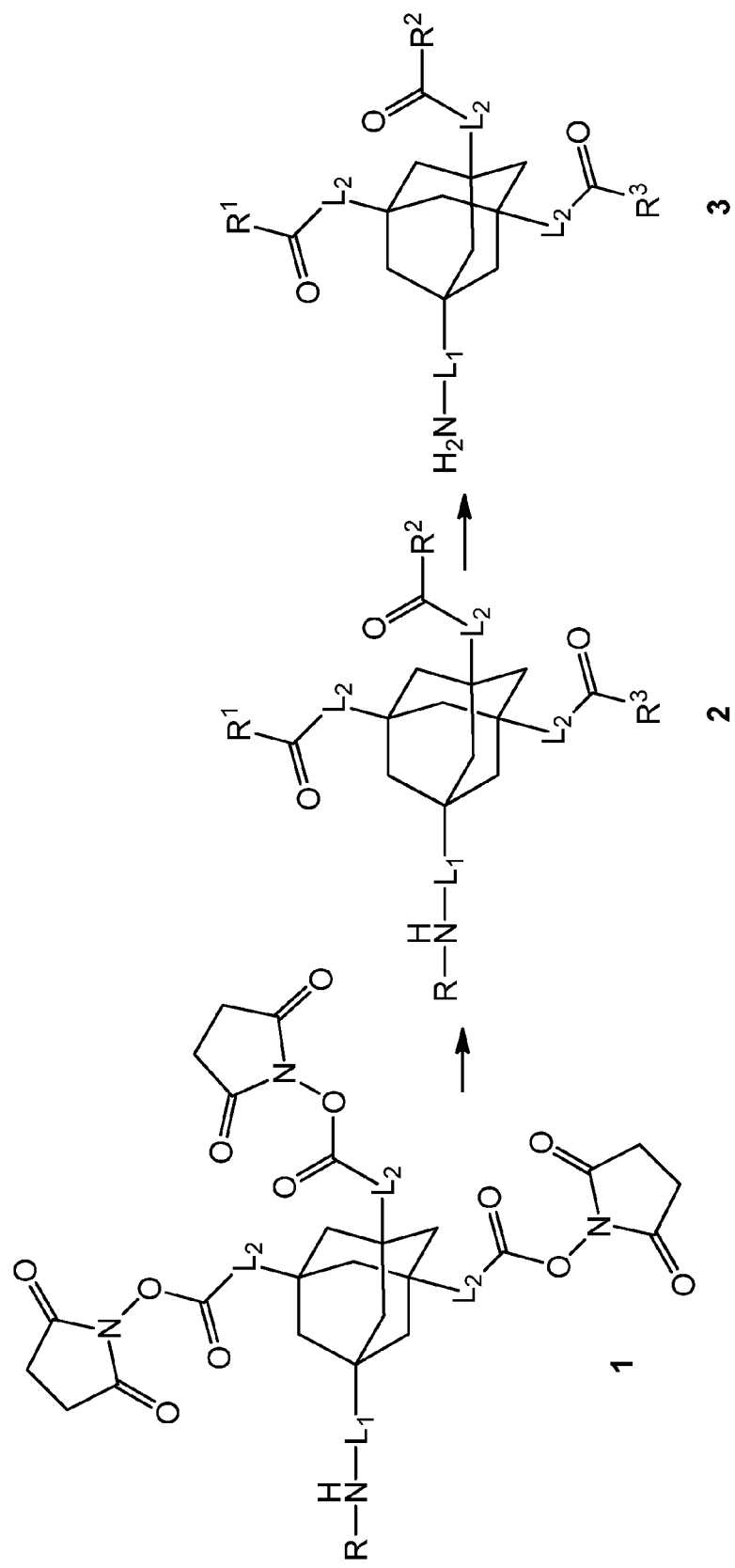
FIG. 1 represents an amine containing targeting ligand conjugated rigid multivalent scaffold.
Figure 2:
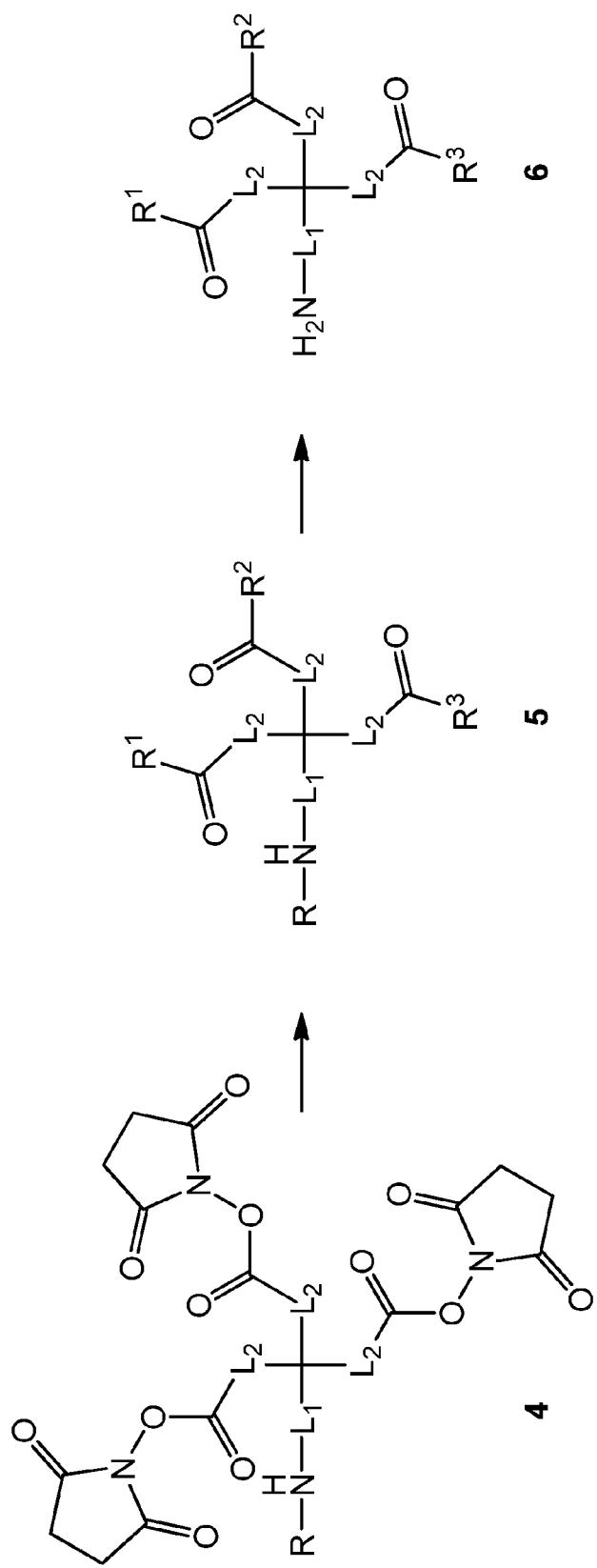
FIG. 2 represents an amine containing targeting ligand conjugated flexible multivalent scaffold.

FIG. 1 and FIG. 2 of present invention describe synthetic scheme for an amine containing targeting ligand conjugated multivalent scaffold. Targeting ligand is conjugated with NHS ester of multivalent scaffold to obtain targeting ligand conjugated multivalent scaffold. Deprotection of an amino protecting group on targeting ligand conjugated multivalent scaffold results in an amine containing targeting ligand conjugated multivalent scaffold.

Figure 3:
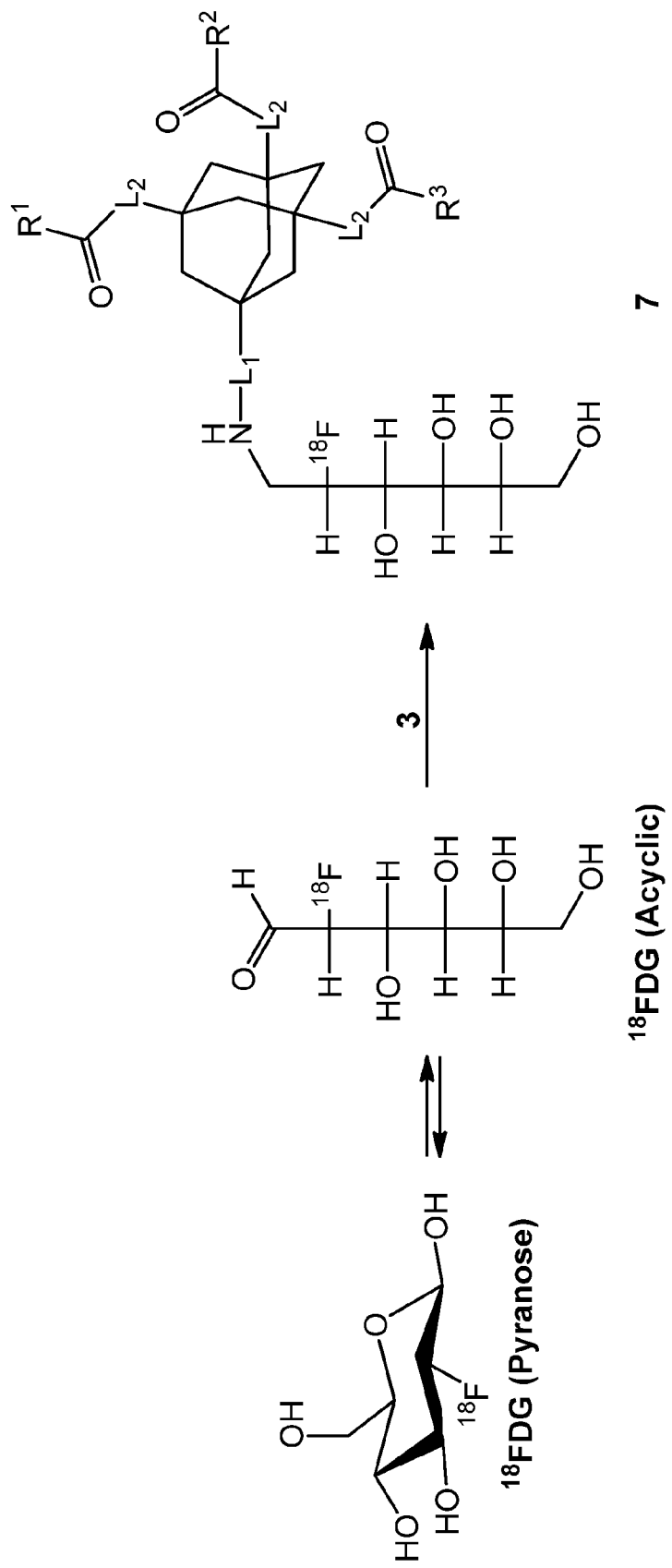
FIG. 3 represents a rigid multivalent $^{18}$FDG amino conjugated imaging agent.
Figure 4:
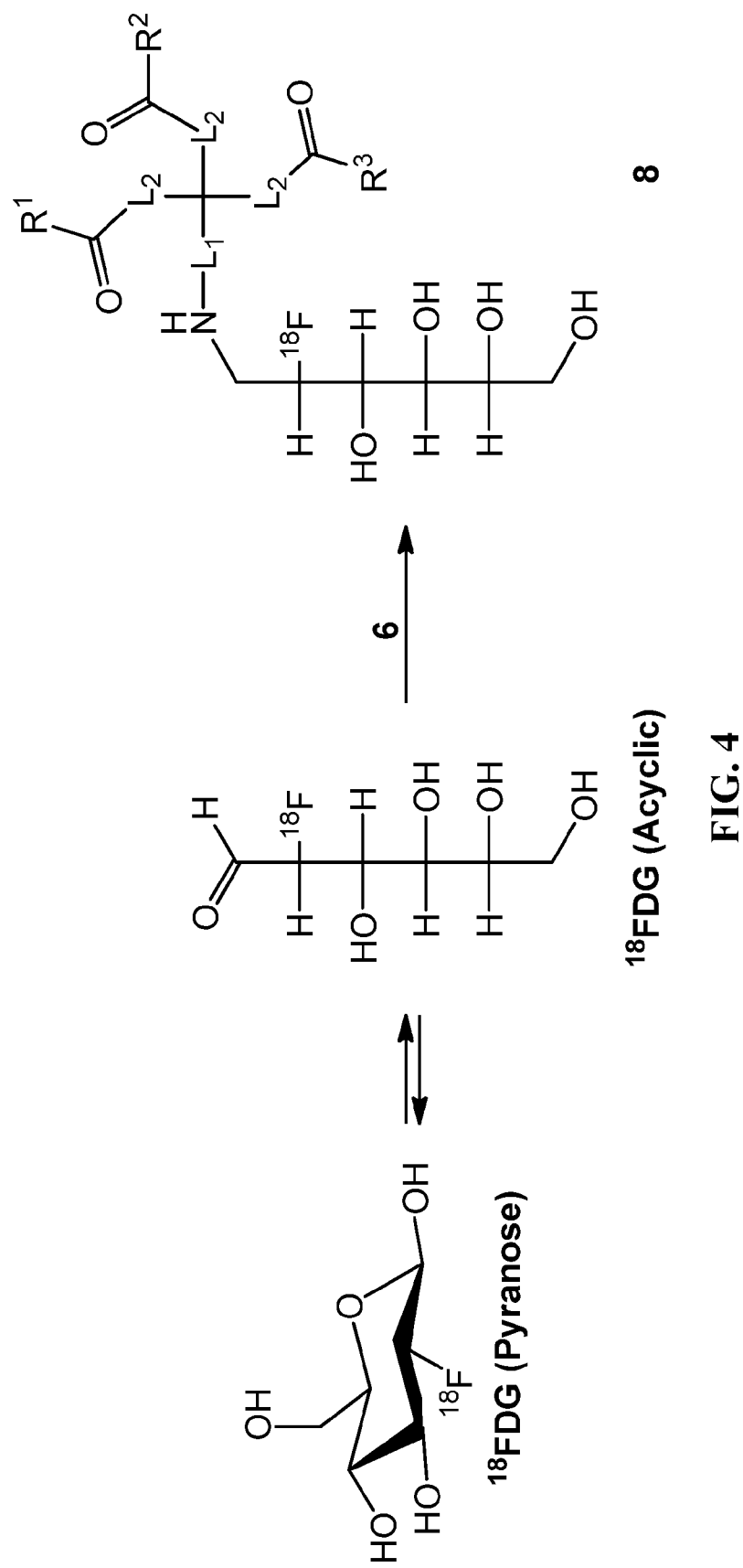
FIG. 4 represents a flexible multivalent $^{18}$FDG amino conjugated imaging agent.

FIG. 3 and FIG. 4 of present invention describe synthetic scheme for a multivalent $^{18}$FDG amino conjugated imaging agent. An amine containing targeting ligand conjugated multivalent scaffold is reacted with $^{18}$FDG in presence of a reducing agent to yield a multivalent $^{18}$FDG amino conjugated imaging agent.

Figure 5:
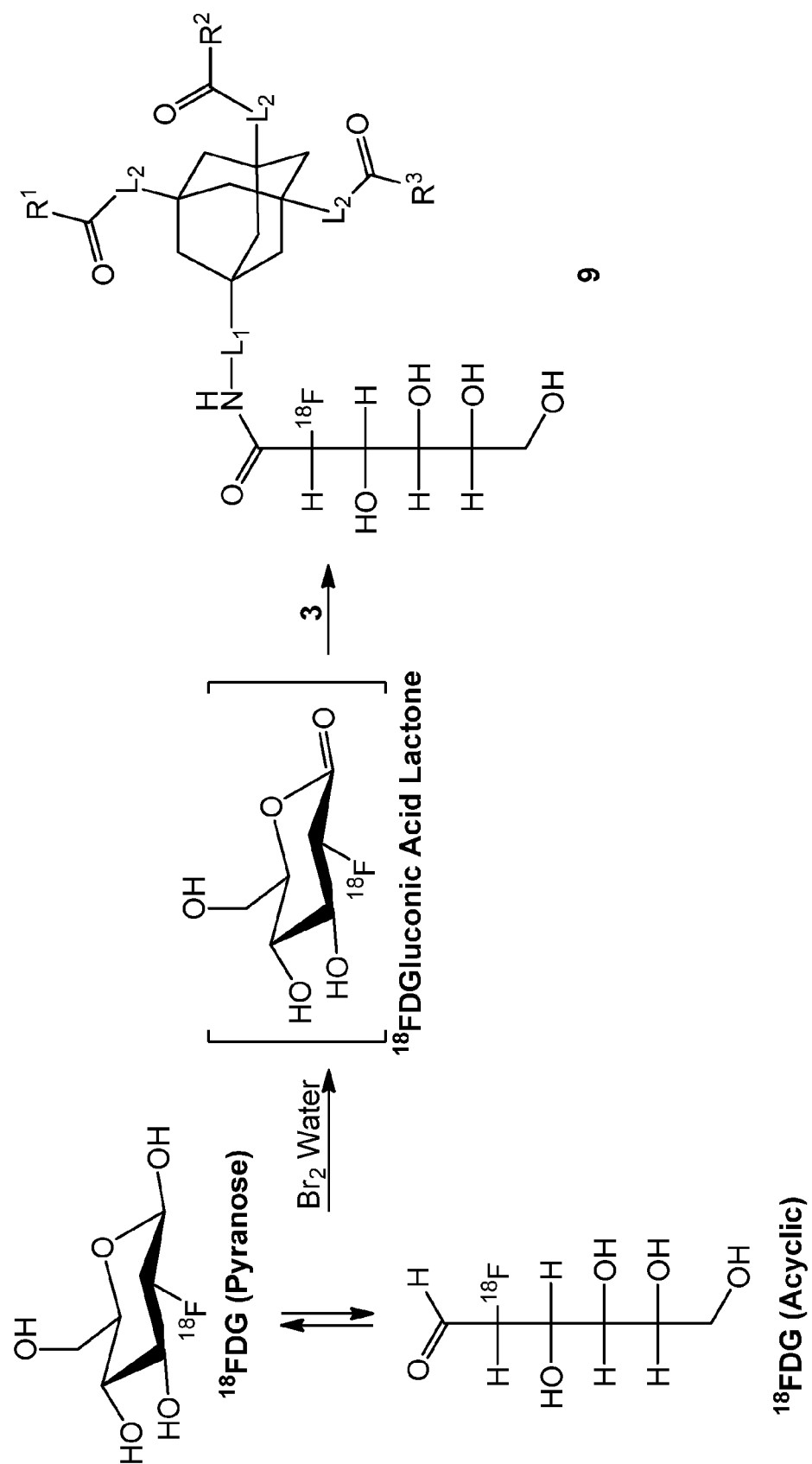
FIG. 5 represents a rigid multivalent $^{18}$FDG amido conjugated imaging agent.
Figure 6:
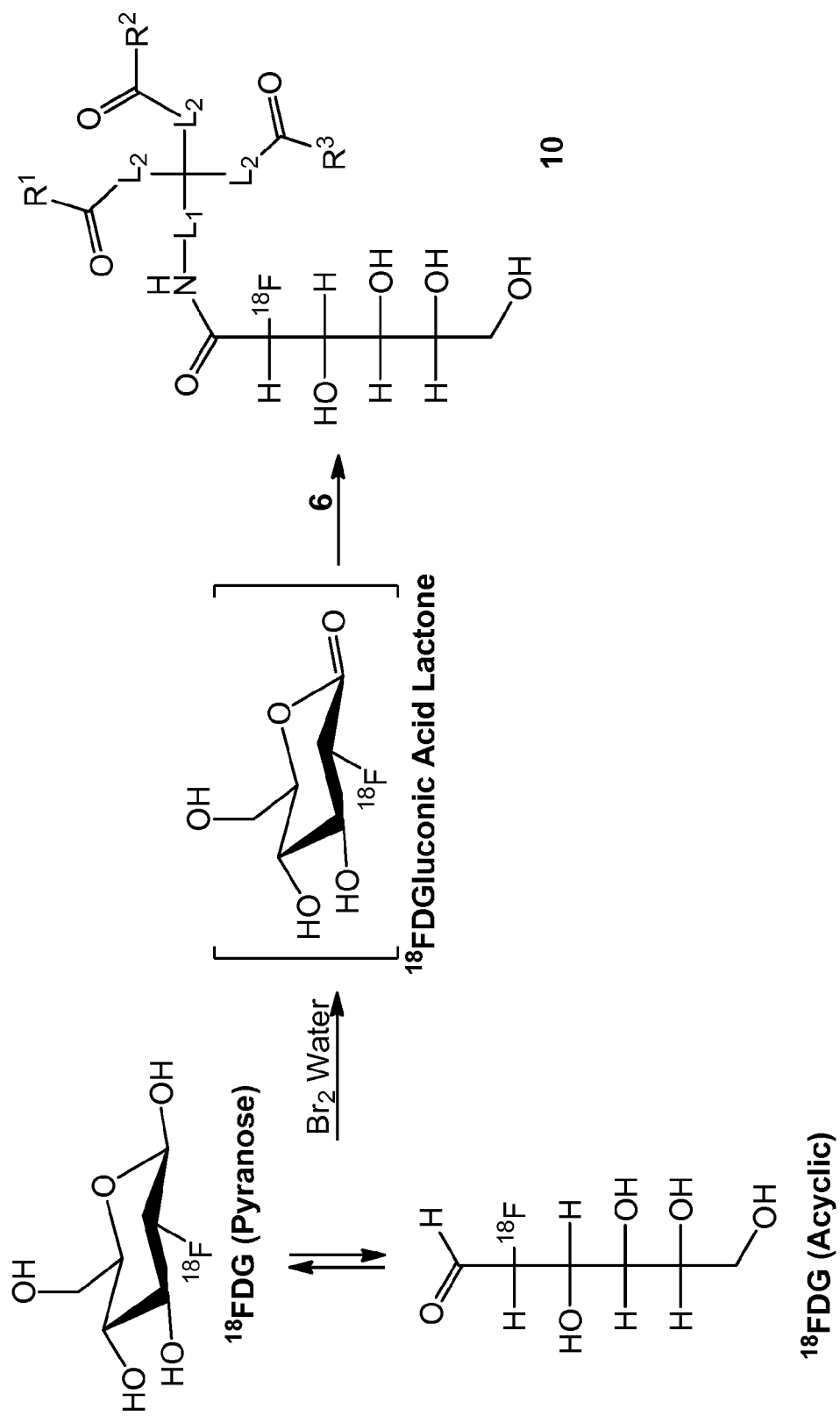
FIG. 6 represents a flexible multivalent $^{18}$FDG amido conjugated imaging agent.

FIG. 5 and FIG. 6 of present invention describe synthetic scheme for a multivalent $^{18}$FDG amido conjugated imaging agent. $^{18}$FDG is treated with bromine water to produce a gluconic acid lactone intermediate. Gluconic acid lactone intermediate is reacted with amine containing targeting ligand conjugated multivalent scaffold to yield a multivalent $^{18}$FDG amido conjugated imaging agent.

In one aspect, the present invention provides a contrast agent having a formula selected from the group of:

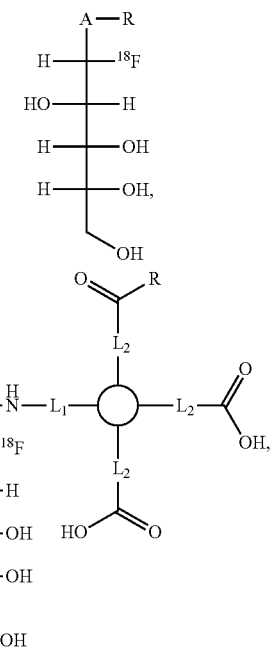

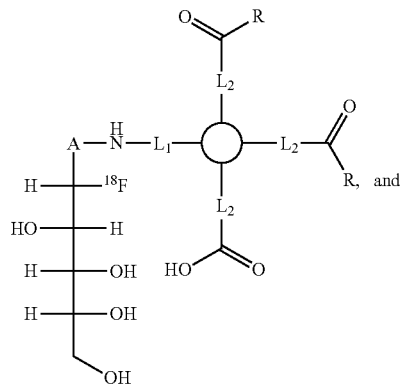

-continued

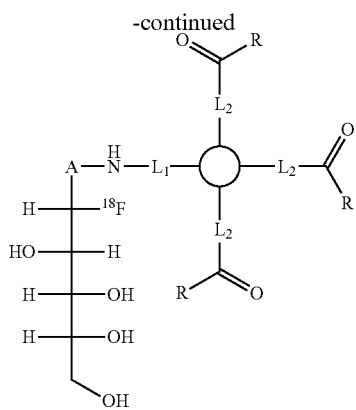

In such an aspect, R is a targeting ligand,
L$_1$ and L$_2$ are linkers,
A is

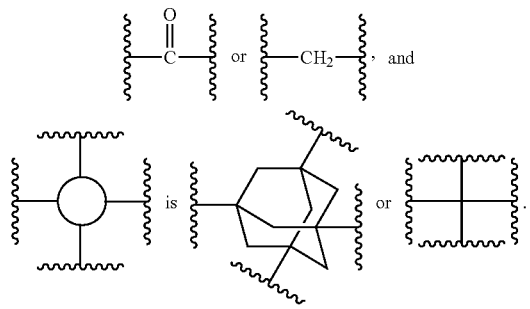

In one embodiment, linkers are independently selected from alkane, amino acid, —NHCO(CH$_2$)$_5$—, polyethylene glycol and polypropylene glycol. In some embodiments, amino acid is natural amino acid. In some embodiments, amino acid is unnatural amino acid. In some embodiments, an alkane is C0-C20 straight chain carbon unit. In some embodiments, polyethylene glycol is 1 to 20 ethylene glycol unit. In some embodiments, polypropylene glycol is 1 to 20 propylene glycol unit. In some embodiments, targeting ligand is independently selected from bisphosphonates, RGD peptides,

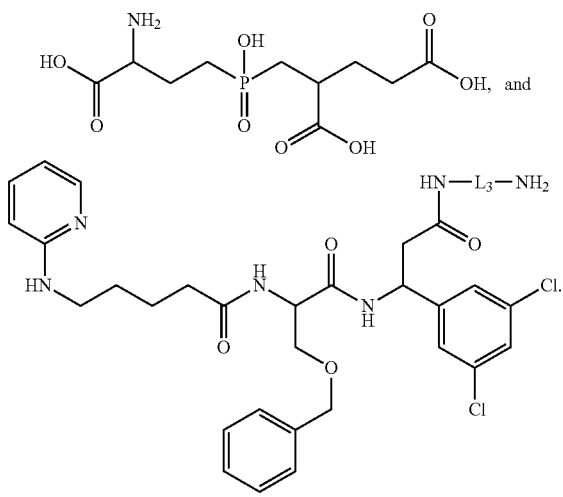

In some embodiments, L$_3$ is a linking moiety independently selected from alkane, polyethylene glycol and polypropylene glycol. In some embodiments, bisphosphonates is selected from alendronate, neridronate, pamidronate, risedronate, tiludronate and zoledronate. In some embodiments, RGD peptides is independently selected from c(RGDfC), c(RADfC), c(RGDfK), c(RADfK), c(RGDfE), c(RADfE), RGDSK, RADSK, RGDS, c(RGDfV), c(RGDyC), c(RADyC), c(RGDyE), c(RGDyK), c(RADyK) and H-E[c(RGDyK)]$_2$.

In an another aspect, the present invention provides a method of making a contrast agent. The method involves steps of:

(a) Starting synthesis with a multivalent scaffold selected from the group of:

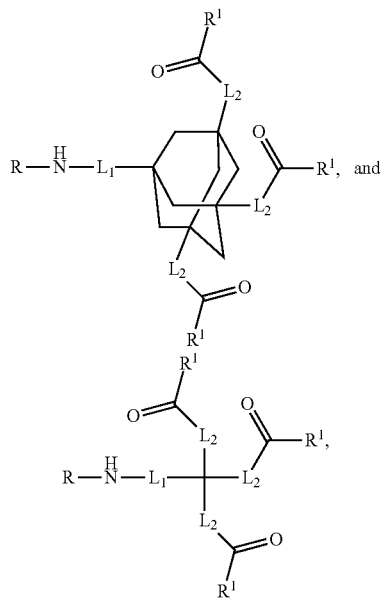

where, R is Boc, Fmoc, Ac, Cbz, Bz or Bn,
L$_1$ and L$_2$ are linkers,
and
R$^1$ is

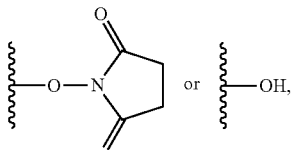

(b) conjugating a multivalent scaffold with a targeting ligand to yield one or more targeting ligand conjugated multivalent scaffold, (c) deprotecting an amino protecting group on one or more targeting ligand conjugated multivalent scaffold to obtain an amine containing targeting ligand conjugated multivalent scaffold, and (d) reacting an amine containing targeting ligand conjugated multivalent scaffold with a $^{18}$FDG in presence of a reducing agent to yield a multivalent $^{18}$FDG amino conjugated imaging agent.

In one embodiment, linkers independently selected from alkane, amino acid, —NHCO(CH$_2$)$_5$—, polyethylene glycol and polypropylene glycol. In some embodiments, amino acid is natural amino acid. In some embodiments, amino acid is unnatural amino acid. In some embodiments, an alkane is C0-C20 straight chain carbon unit. In some embodiments, polyethylene glycol is 1 to 20 ethylene glycol unit. In some embodiments, polypropylene glycol is 1 to 20 propylene glycol unit. In some embodiments, targeting ligand is independently selected from bisphosphonates, RGD peptides,

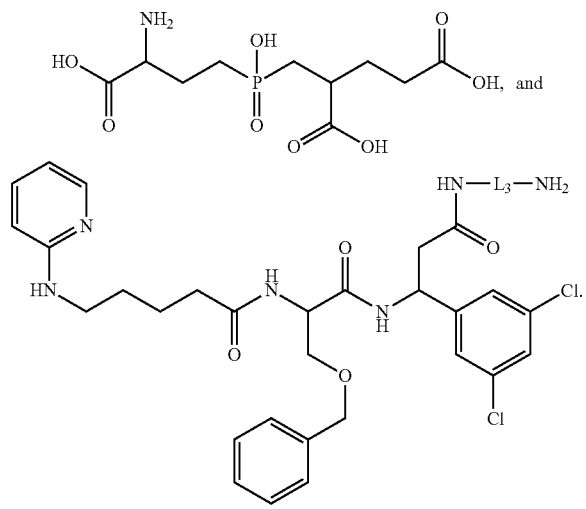

In some embodiments, $L_3$ is a linking moiety independently selected from alkane, polyethylene glycol and polypropylene glycol. In some embodiments, bisphosphonates is selected from alendronate, neridronate, pamidronate, risedronate, tiludronate and zoledronate. In some embodiments, RGD peptides is independently selected from c(RGDfC), c(RADfC), c(RGDfK), c(RADfK), c(RGDfE), c(RADfE), RGDSK, RADSK, RGDS, c(RGDfV), c(RGDyC), c(RADyC), c(RGDyE), c(RGDyK), c(RADyK) and H-E[c(RGDyK)]$_2$. In some embodiments, a reducing agent is independently selected from sodium cyanoborohydride, lithium cyanoborohydride, tetrabutylammonium cyanoborohydride, sodium triacetoxyborohydride, tetramethylammonium triacetoxyborohydride, sodium borohydride, lithium borohydride, potassium borohydride, polymer supported borohydride, 2-picoline-borane and borane-pyridine.

In an another aspect, the present invention provides a method of making a contrast agent. The method involves steps of:
(a) Starting synthesis with a multivalent scaffold selected from the group of:

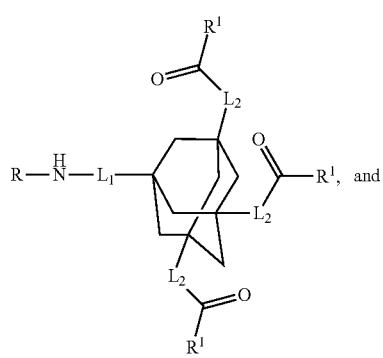

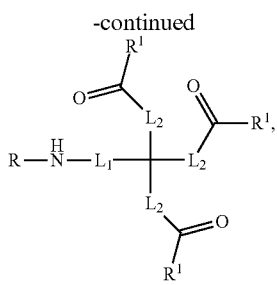

where, R is Boc, Fmoc, Ac, Cbz, Bz or Bn,
$L_1$ and $L_2$ are linkers,
and
$R^1$ is

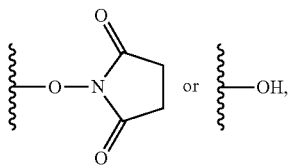

(b) conjugating a multivalent scaffold with a targeting ligand to yield one or more targeting ligand conjugated multivalent scaffold, (c) deprotecting an amino protecting group on one or more targeting ligand conjugated multivalent scaffold to obtain an amine containing targeting ligand conjugated multivalent scaffold, (d) treating a $^{18}$FDG with a bromine water to produce a gluconic acid lactone intermediate, and (e) reacting a gluconic acid lactone intermediate with an amine containing targeting ligand conjugated multivalent scaffold to yield a multivalent $^{18}$FDG amido conjugated imaging agent.

In one embodiment, linkers independently selected from alkane, amino acid, —NHCO(CH$_2$)$_5$—, polyethylene glycol and polypropylene glycol. In some embodiments, amino acid is natural amino acid. In some embodiments, amino acid is unnatural amino acid. In some embodiments, an alkane is C0-C20 straight chain carbon unit. In some embodiments, polyethylene glycol is 1 to 20 ethylene glycol unit. In some embodiments, polypropylene glycol is 1 to 20 propylene glycol unit. In some embodiments, targeting ligand is independently selected from bisphosphonates, RGD peptides,

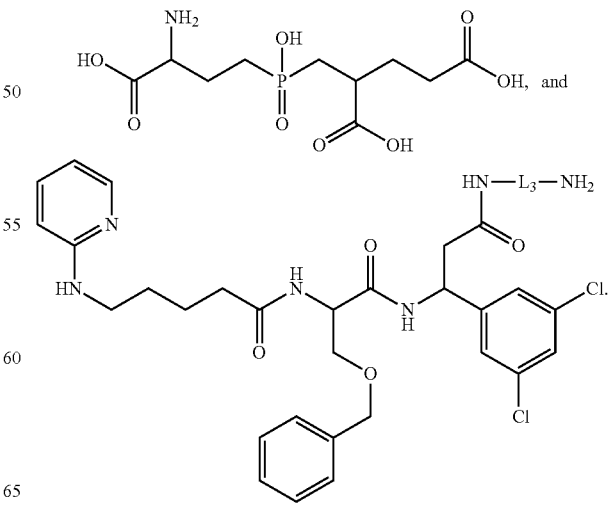

In some embodiments, $L_3$ is a linking moiety independently selected from alkane, polyethylene glycol and polypropylene glycol. In some embodiments, bisphosphonates is selected from alendronate, neridronate, pamidronate, risedronate, tiludronate and zoledronate. In some embodiments, RGD peptides is independently selected from c(RGDfC), c(RADfC), c(RGDfK), c(RADfK), c(RGDfE), c(RADfE), RGDSK, RADSK, RGDS, c(RGDfV), c(RGDyC), c(RADyC), c(RGDyE), c(RGDyK), c(RADyK) and H-E[c(RGDyK)]$_2$.

The $^{18}$FDG-based PET multivalent radiotracers generated by present invention can be used for, e.g., PET, radioimmuno, and magnetic resonance applications for detection, imaging and treatment of cancers and other abnormalities. In particular, $^{18}$FDG-based PET multivalent radiotracers generated by present invention are specific for bone metastases, prostate-specific membrane antigen, and integrins such as $\alpha_v\beta_3$ and $\alpha_v\beta_6$. Specifically, bisphosphontes, a multivalent pamidronate $^{18}$FDG conjugated imaging agent have specificity over clinically used Na$^{18}$F.

To determine the selectivity and specificity of $^{18}$FDG amino-Ad-Pam-Monomer for hydroxyapatite (HA), a major mineral component of calcifications and normal bone, over other calcium salts, in the present invention an incubation of equal quantity each of Ca-hydroxyapatite (HA), Ca-pyrophosphate (CPP), Ca-phosphate (CP), Ca-oxalate (CO), and Ca-carbonate (CC) salts with $^{18}$FDG amino-Ad-Pam-Monomer in phosphate buffered saline (PBS) is performed. PET/CT images are acquired after incubation and washing of crystals, $^{18}$FDG amino-Ad-Pam-Monomer has about 5-fold specificity for HA over other calcium salts found in the body and permits PET/CT detection of HA with high sensitivity. However, Na$^{18}$F, the Food and Drug Administration approved imaging agent for bone scintigraphy, permits about 1.5 fold specificity for HA over other calcium salts.

Examples

Figure 7:
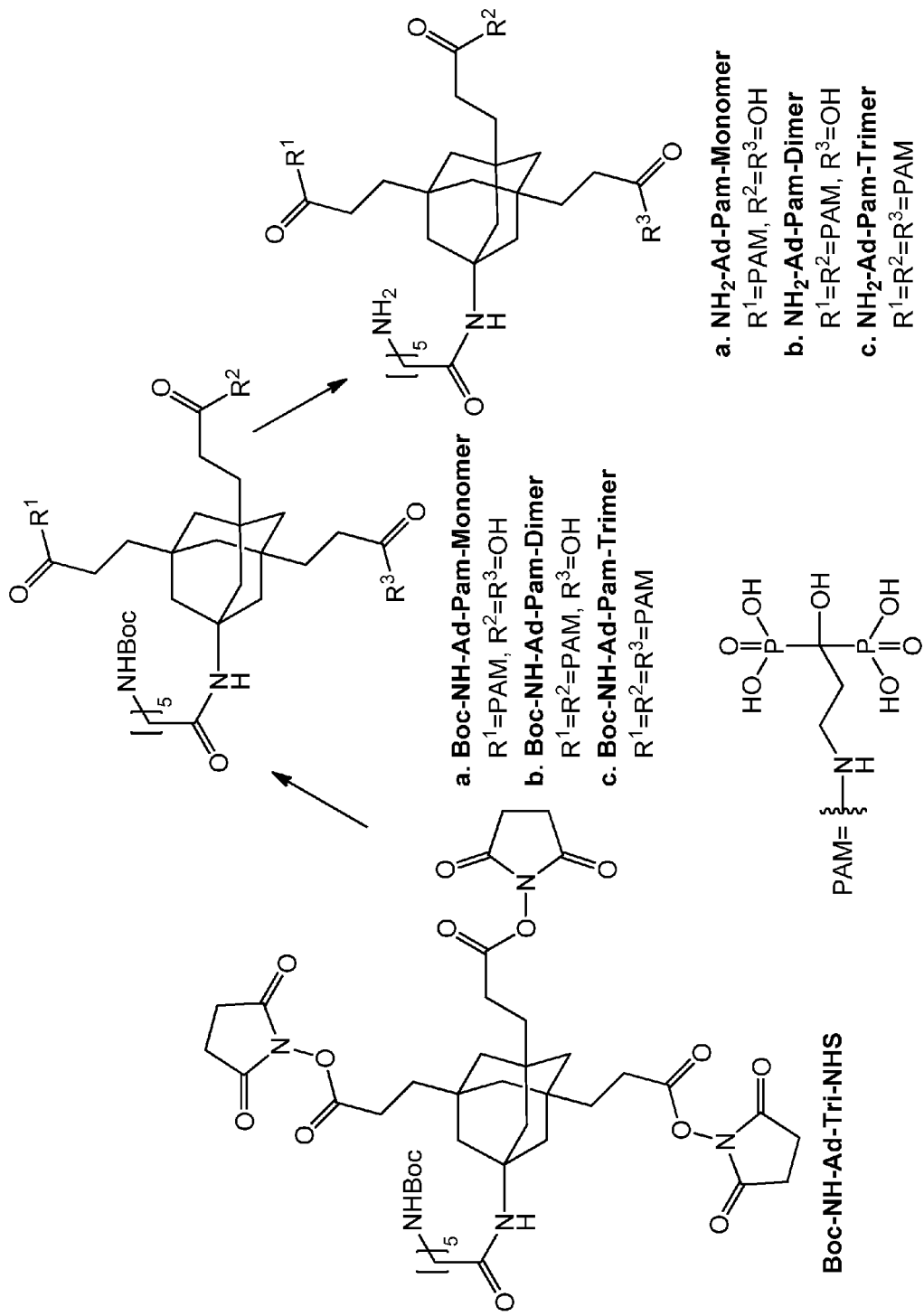
FIG. 7 represents a synthetic scheme for preparation of NH$_2$-Ad-Pam-Monomer, NH$_2$-Ad-Pam-Dimer, and NH$_2$-Ad-Pam-Trimer.

1. Preparation of NH$_2$-Ad-Pam-Monomer (FIG. 7)

Boc-NH$_2$-Ad-Pam-Monomer

To a solution of pamidronic acid (0.04 mmol) in 0.4 mL water and dimethyl formamide (DMF; 0.4 mL) at room temperature (RT), is added triethylamine (TEA, 0.25 mmol) followed by dropwise addition of Boc-NH-Ad-Tri-NHS (0.01 mmol) {Humblet, 2009} in dimethylformamide (DMF; 0.2 mL) for 5 min and stirring is continued for 16 h. The reaction mixture is poured over 2 mL ice-cold water and purified by preparative HPLC to yield Boc-NH-Ad-Pam-Monomer (37%), Boc-NH-Ad-Pam-Dimer (25%), and Boc-NH-Ad-Pam-Trimer (15%).

NH$_2$-Ad-Pam-Monomer

Boc-NH-Ad-Pam-Monomer (0.01 mmol) is taken in trifluoroacetic acid (TFA; 1 mL). The solution is stirred at RT for 2.5 h then the acid is removed by a N$_2$ stream. After lyophilization, NH$_2$-Ad-Pam-Monomer is obtained without further purification.

Figure 8:
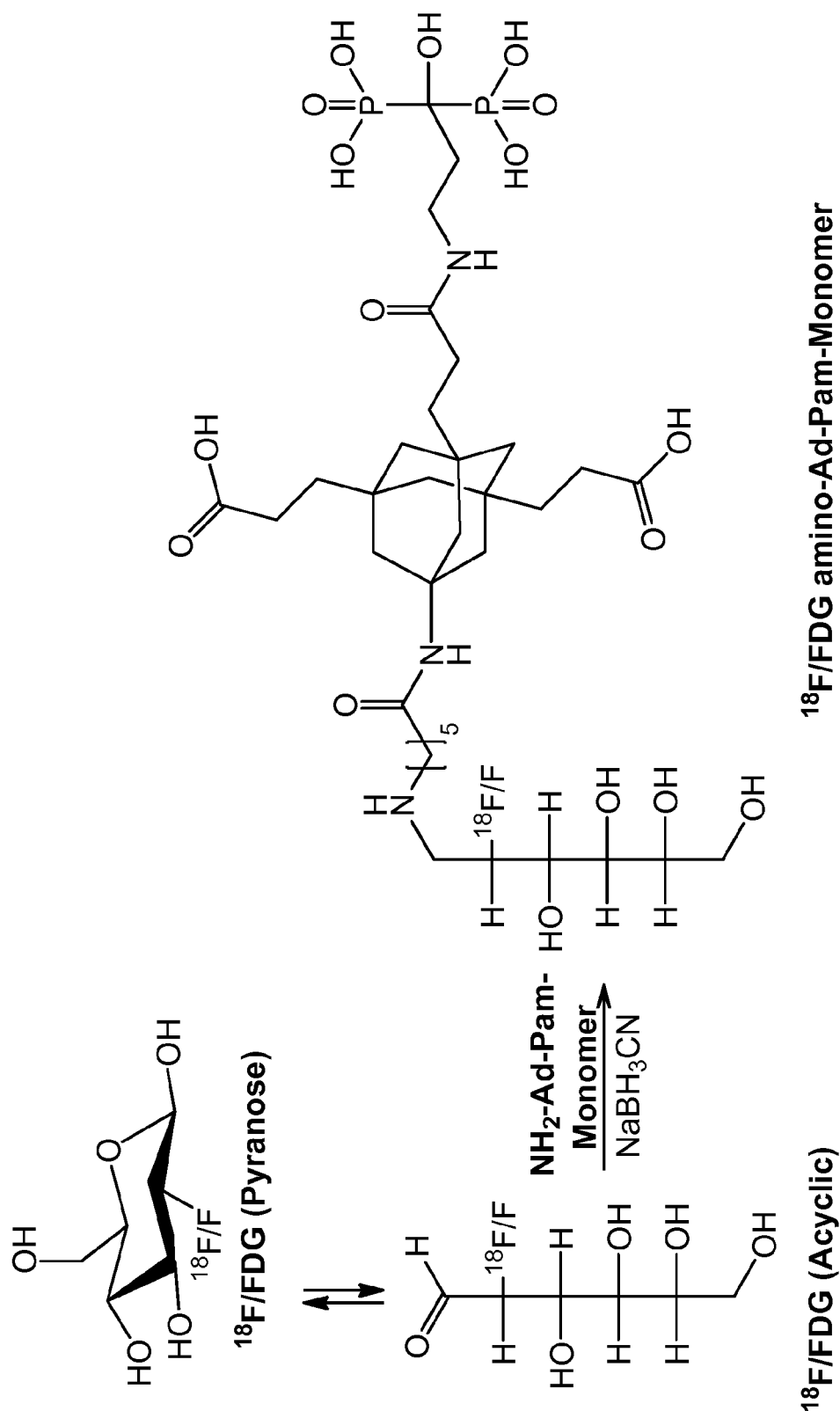
FIG. 8 represents a synthetic scheme for preparation of $^{18}$F/FDG amino-Ad-Pam-Monomer.

2. Preparation of $^{18}$F/FDG amino-Ad-Pam-Monomer (FIG. 8)

NH$_2$-Ad-Pam-Monomer (0.012 mmol) in 0.3 mL water/methanol (1/2) and cold FDG (0.01 mmol) in 0.2 mL water are mixed in a 4 mL Teflon capped tube fitted with stirring bar. Sodium cyanoborohydride (0.012 mmol) in 0.1 mL methanol is added and the tube is mounted and agitated in a CEM Explorer microwave system at 75-110 0° C. for 15-20 min. Progress of the reaction is monitored by LCMS. After completion, the reaction mixture is poured over 2 mL of ice-cold water and purified by HPLC to result in FDG amino-Ad-Pam-Monomer (40% yield). Similarly, NH$_2$-Ad-Pam-Monomer is reacted with $^{18}$FDG in the same conditions to afford $^{18}$FDG amino-Ad-Pam-Monomer in 35-40% radiochemical yield.

Figure 9:
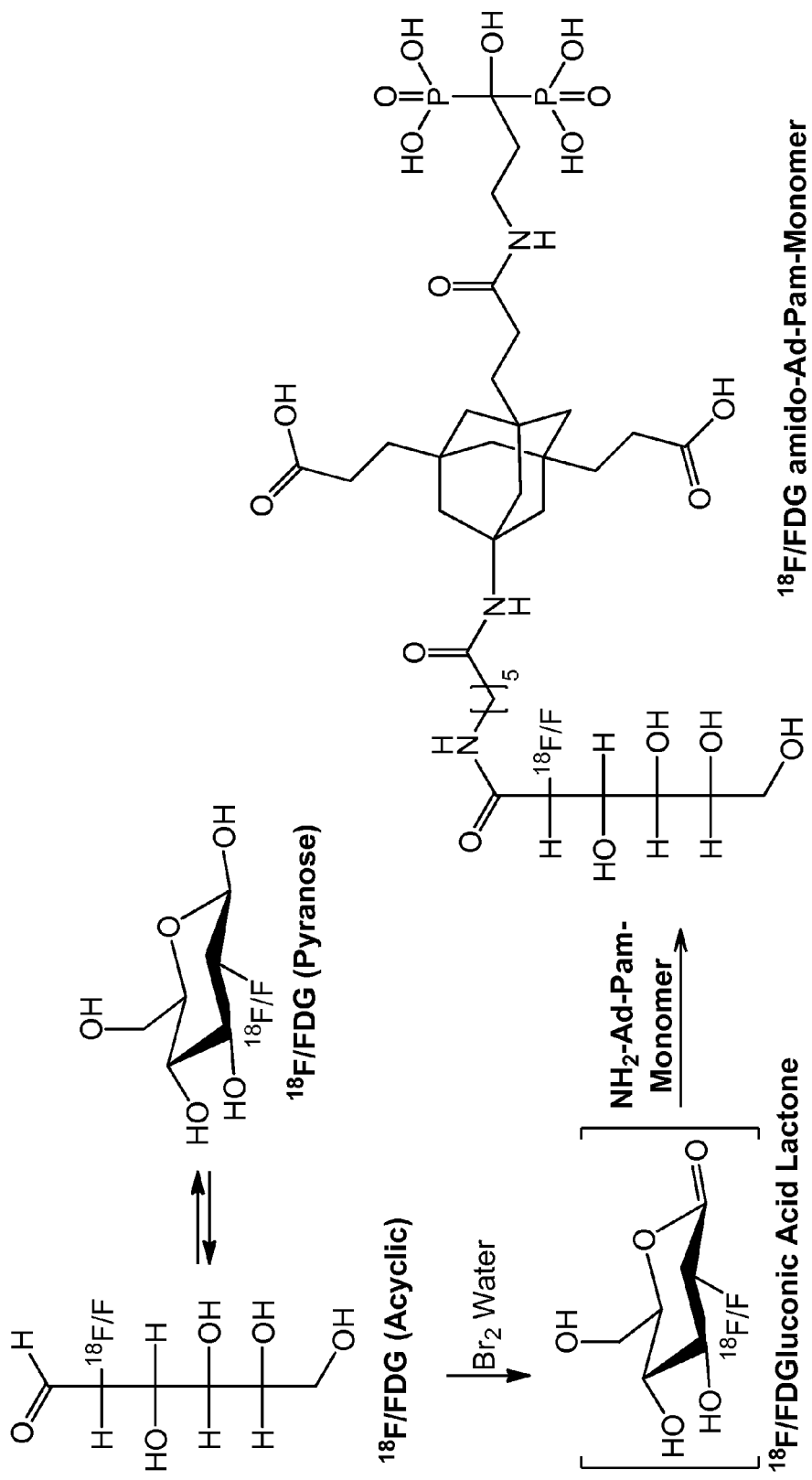
FIG. 9 represents a synthetic scheme for preparation of $^{18}$F/FDG amido-Ad-Pam-Monomer.

3. Preparation of $^{18}$F/FDG amido-Ad-Pam-Monomer (FIG. 9)

Cold FDG stock solution (20 µL, 50 nM) is taken in a glass scintillation vial, added bromine water (200 µA, 200 nM), and vortexed this mixture for 2 min. Phosphate buffered saline (PBS, 100 µL, 100 nM, pH 6.5) is added and vortexed for 15 min. Mineral oil (1000 µL) is added to quench the excess bromine. Once the aqueous layer is colorless quenching is complete. Aqueous layer is carefully pipetted out into a clean vial. To this aqueous layer, MeOH (300 µL) is added under ice-cold water with stirring, subsequently NH$_2$-Ad-Pam-Monomer (20 µL, 0.5 µM) is added and stirring is continued for 20 min. The product FDG amido-Ad-Pam-Monomer obtained is analyzed by LCMS and purified by HPLC. Similarly, $^{18}$FDG is oxidized by bromine water and is reacted with NH$_2$-Ad-Pam-Monomer in the same condition to afford $^{18}$FDG amido-Ad-Pam-Monomer in 40-45% radiochemical yield.

4. In Vitro Calcium Salt Specificity Experiments

In a 96-well plate, 5 mg/mL of hydroxyapatite (HA) or the phosphate, oxalate, carbonate, and pyrophosphate salts of calcium are separately incubated with $^{18}$FDG amino-Ad-Pam-Monomer (10 µCi) in 100 µL PBS for 20 min with continuous vortexing at RT. Crystals are washed 4 times with a 100-fold excess of PBS, centrifuged and mounted on PET/CT and 10 minute static scans are acquired. Similarly, calcium salt binding study is performed with Na$^{18}$F in a same condition.

REFERENCES

1. Raichle, M. E. Quantitative in vivo autoradiography with positron emission tomography. *Brain Res.* 1979, 180, 47-68.
2. Yamaoto, Y. L.; Thompson, C. J.; Diksic, M.; Meyer, E.; Feindel, W. H. Positron emission tomography. *Neurosurg. Rev.* 1984, 7, 233-252.
3. Kelloff, G. J; Hoffman, J. M.; Johnson, B.; et al. Progress and promise of FDG-PET imaging for cancer patient management and oncologic drug development. *Clin. Cancer Res.* 2005, 11, 2785-2808.
4. Kumar, R. A.; Chauhan, H.; Zhuang, M.; Chandra, P.; Schnall, M.; alavi, A. Standardized uptake values of normal breast tissue with 2-deoxy-2[F-18]fluoro-D-glucose positron emission tomography: variations with age, breast density, and menopausal status. *Mol. Imaging. Biol.* 2006, 8, 355-362.

5. Conti, M.; Bendriem, B.; Casey, M.; Chen, M.; Kehren, F.; Michel, C.; Panin, V. First experimental results of time-of-flight reconstruction on an LSO PET scanner. *Phys. Med. Biol.* 2005, 50, 4507-4526.

6. Surti. S.; Karp, J. S.; Popescu, L. M.; Daube-Witherspoon, M. E.; Werner, M. Investigation of time-of-flight benefit for fully 3-D PET. *IEEE Trans Med. Imaging* 2006, 25, 529-538.

7. Kitov, P. I.; Bundle, D. R. On the nature of the multivalency effect: a thermodynamic model. *J. Am. Chem. Soc.* 2003, 125, 16271-16284.

8. Mammen, M.; Chio, S.-K.; Whitesides, G. M. Polyvalent interactions in biological systems: implications for design and use of multivalent ligands and inhibitors. *Angew. Chem., Int. Ed.* 1998, 37, 2755-2794.

9. Lundquist, J. J.; Toone, E. J. The cluster glycoside effect. *Chem. Rev.* 2002, 102, 555-578.

10. Lindhorst, T. K. Artificial multivalent sugar ligands to understand and manipulate carbohydrate-protein interactions. *Top. Curr. Chem.* 2002, 218, 201-235.

11. Wright, D.; Usher, L. Multivalent binding in the design of bioactive compounds. *Curr. Org. Chem.* 2001, 5, 1107-1131.

12. Carlson, C.; Mowery, P.; Owen, R.; Dykhuizen, E.; Kiessling, L. Selective tumor cell targeting using low-affinity, multivalent interactions. *ACS Chem. Biol.* 2007, 2, 119-127.

13. Thumshirn, G.; Hersel, U.; Goodman, S. L.; Kessler, H. Multimeric cyclic RGD peptides as potential tools for tumor targeting: solid-phase peptide synthesis and chemoselective oxime ligation. *Chem. sEur. J.* 2003, 9, 2717-2725.

14. Voegtle, F.; Richardt, G.; Werner, N. Dendritische Moleku"le; B. G. Teubner Verlag: Wiesbaden, Germany, 2007.

15. Haag, R.; Kratz, F. Polymer therapeutics: concepts and applications. *Angew. Chem., Int. Ed.* 2006, 45, 1198-1215.

16. Humblet, V.; Misra, P.; Bhushan, K. R.; et al. Multivalent scaffolds for affinity maturation of small molecule cell surface binders and their application to prostate tumor targeting. *J. Med. Chem.* 2009, 52, 544-550.

What is claimed is:

1. A contrast agent having a formula selected from the group consisting of:

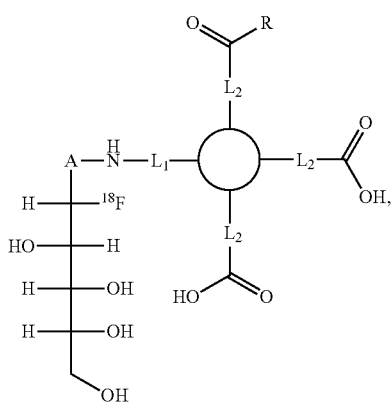

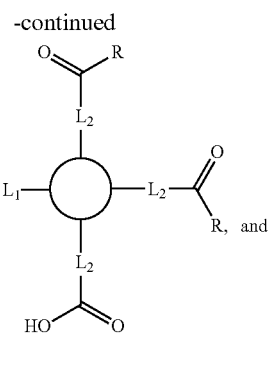

-continued

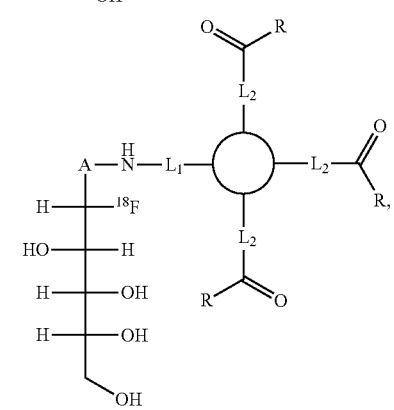

wherein

R is a targeting ligand;

$L_1$ and $L_2$ are linkers;

A is

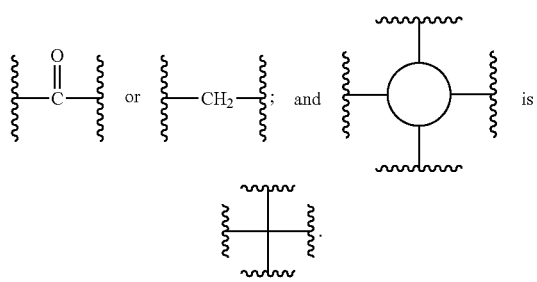

2. The contrast agent of claim 1, wherein said linkers are selected from the group consisting of alkane, amino acid, —NHCO(CH$_2$)$_5$—, polyethylene glycol and polypropylene glycol.

3. The contrast agent of claim 1, wherein said contrast agent is in a form of pharmaceutically acceptable salts, hydrates and solvents.

4. The contrast agent of claim 1, wherein $L_1$ and $L_2$ may be same or different.

5. The contrast agent of claim 1, wherein said targeting ligand is independently selected from the group consisting of a bisphosphonate, an RGD peptide

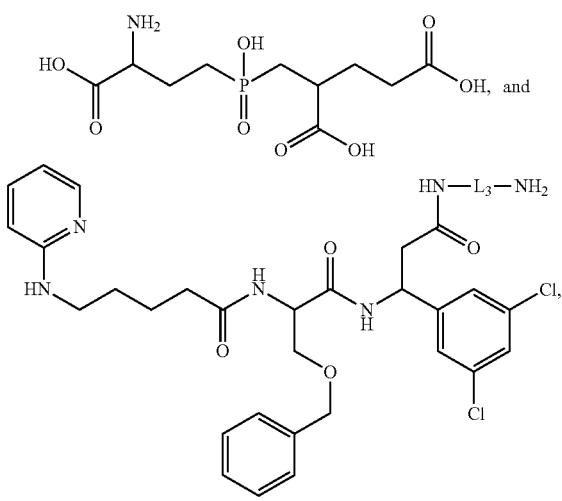

wherein L₃ is a linking moiety independently selected from the group consisting of alkane, polyethylene glycol and polypropylene glycol.

6. The contrast agent of claim 5, wherein said bisphosphonate is independently selected from the group consisting of alendronate, etidronate, ibandronate, incadronate, neridronate, olpadronate, phosphonate, pamidronate, risedronate, tiludronate and zoledronate.

7. The contrast agent of claim 5, wherein said RGD peptide is independently selected from the group consisting of c(RGDfC), c(RADfC), c(RGDfK), c(RADfK), c(RGDfE), c(RADfE), RGDSK, RADSK, RGDS, c(RGDfV), c(RGDyC), c(RADyC), c(RGDyE), c(RGDyK), c(RADyK) and H-E[c(RGDyK)]₂.

8. A method of making a contrast agent, said method comprising:
(a) providing a multivalent scaffold, wherein said multivalent scaffold is

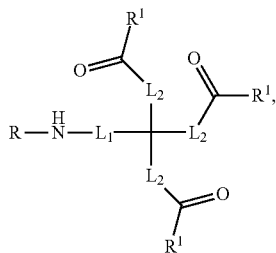

wherein
R is Boc, Fmoc, Ac, Cbz, Bz or Bn;
L₁ and L₂ are linkers;
and
R¹ is

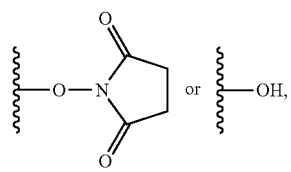

(b) conjugating said multivalent scaffold with a targeting ligand to yield one or more targeting ligand conjugated multivalent scaffold;
(c) deprotecting an amino protecting group on said one or more targeting ligand conjugated multivalent scaffold to obtain an amine containing targeting ligand conjugated multivalent scaffold;
(d) reacting said amine containing targeting ligand conjugated multivalent scaffold with a 2-[$^{18}$F]fluoro-2-deoxy-D-glucose in presence of a reducing agent to yield a multivalent $^{18}$FDG amino conjugated imaging agent.

9. The method of claim 8, wherein said linkers are selected from the group consisting of alkane, amino acid, —NHCO(CH₂)₅—, polyethylene glycol and polypropylene glycol.

10. The method of claim 8, wherein said contrast agent is in a form of pharmaceutically acceptable salts, hydrates and solvents.

11. The method of claim 8, wherein said reducing agent is selected from the group consisting of sodium cyanoborohydride, lithium cyanoborohydride, tetrabutylammonium cyanoborohydride, sodium triacetoxyborohydride, tetramethylammonium triacetoxyborohydride, sodium borohydride, lithium borohydride, potassium borohydride, polymer supported borohydride, 2-picoline-borane and borane-pyridine.

12. The method of claim 8, wherein said targeting ligand is independently selected from the group consisting of a bisphosphonate, an RGD peptide

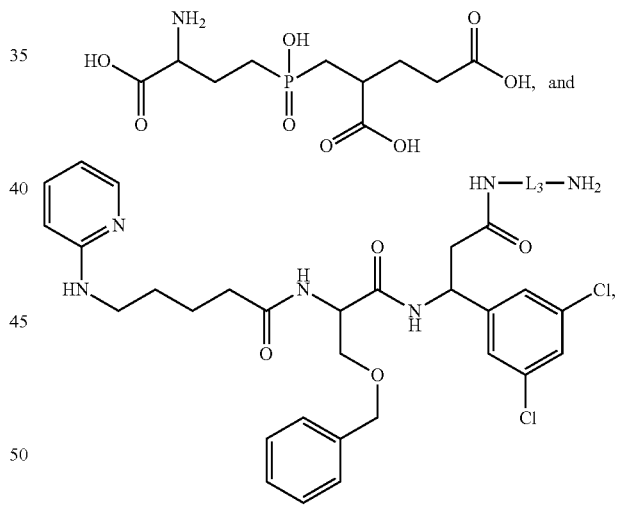

wherein L₃ is a linking moiety independently selected from the group consisting of alkane, polyethylene glycol and polypropylene glycol.

13. The method of claim 12, wherein said bisphosphonate is independently selected from the group consisting of alendronate, etidronate, ibandronate, incadronate, neridronate, olpadronate, phosphonate, pamidronate, risedronate, tiludronate and zoledronate.

14. The method of claim 12, wherein said RGD peptide is independently selected from the group consisting of c(RGDfC), c(RADfC), c(RGDfK), c(RADyK), c(RGDfE), c(RADfE), RGDSK, RADSK, RGDS, c(RGDfV), c(RGDyC), c(RADyC), c(RGDyE), c(RGDyK), c(RADyK), and H-E[c(RGDyK)]₂.

15. A method of making a contrast agent, said method comprising:
(a) providing a multivalent scaffold, wherein said multivalent scaffold is

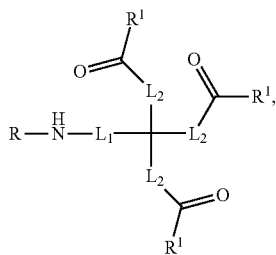

wherein
R is Boc, Fmoc, Ac, Cbz, Bz or Bn;
$L_1$ and $L_2$ are linkers;
and
$R^1$ is

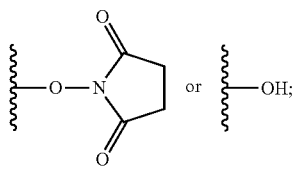

(b) conjugating said multivalent scaffold with a targeting ligand to yield one or more targeting ligand conjugated multivalent scaffold;
(c) deprotecting an amino protecting group on said one or more targeting ligand conjugated multivalent scaffold to obtain an amine containing targeting ligand conjugated multivalent scaffold;
(d) treating a 2-[$^{18}$F]fluoro-2-deoxy-D-glucose with a bromine water to produce a gluconic acid lactone intermediate;
(e) reacting said gluconic acid lactone intermediate with said amine containing targeting ligand conjugated multivalent scaffold to yield a multivalent $^{18}$FDG amido conjugated imaging agent.

16. The method of claim 15, wherein said linkers are selected from the group consisting of alkane, amino acid, —NHCO(CH$_2$)$_5$—, polyethylene glycol and polypropylene glycol.

17. The method of claim 15, wherein said contrast agent is in a form of pharmaceutically acceptable salts, hydrates and solvents.

18. The method of claim 15, wherein said targeting ligand is independently selected from the group consisting of a bisphosphonate, an RGD peptide

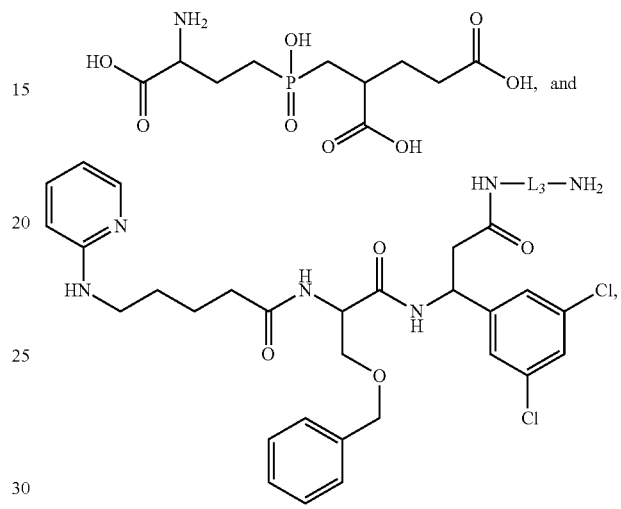

wherein $L_3$ is a linking moiety independently selected from the group consisting of alkane, polyethylene glycol and polypropylene glycol.

19. The method of claim 18, wherein said bisphosphonate is independently selected from the group consisting of alendronate, etidronate, ibandronate, incadronate, neridronate, olpadronate, phosphonate, pamidronate, risedronate, tiludronate and zoledronate.

20. The method of claim 18, wherein said RGD peptide is independently selected from the group consisting of c(RGDfC), c(RADfC), c(RGDfK), c(RADfK), c(RGDfE), c(RADfE), RGDSK, RADSK, RGDS, c(RGDfV), c(RGDyC), c(RADyC), c(RGDyE), c(RGDyK), c(RADyK), and H-E[c(RGDyK)]$_2$.

* * * * *